United States Patent
Branton-Housley

(10) Patent No.: US 9,832,530 B2
(45) Date of Patent: Nov. 28, 2017

(54) REDUCE BLUE LIGHT AT SET-TOP BOX TO ASSIST WITH SLEEP

(71) Applicant: EchoStar Technologies L.L.C., Englewood, CO (US)

(72) Inventor: Simon Branton-Housley, Fort Collins, CO (US)

(73) Assignee: EchoStar Technologies L.L.C., Englewood, CO (US)

( * ) Notice: Subject to any disclaimer, the term of this patent is extended or adjusted under 35 U.S.C. 154(b) by 0 days.

(21) Appl. No.: 15/143,954

(22) Filed: May 2, 2016

(65) Prior Publication Data

US 2017/0318345 A1    Nov. 2, 2017

(51) Int. Cl.
| | |
|---|---|
| H04N 21/485 | (2011.01) |
| H04N 21/478 | (2011.01) |
| H04N 21/61 | (2011.01) |
| H04N 9/73 | (2006.01) |
| G09G 5/02 | (2006.01) |

(52) U.S. Cl.
CPC ............. *H04N 21/478* (2013.01); *G09G 5/02* (2013.01); *H04N 9/735* (2013.01); *H04N 21/6143* (2013.01); *G09G 2320/0666* (2013.01)

(58) Field of Classification Search
None
See application file for complete search history.

(56) References Cited

U.S. PATENT DOCUMENTS

| | | | | |
|---|---|---|---|---|
| 2015/0062186 A1* | 3/2015 | Park | ..................... | G09G 3/3225 345/690 |
| 2015/0348468 A1* | 12/2015 | Chen | .................... | G09G 3/3413 345/207 |
| 2016/0277244 A1* | 9/2016 | Reichert, Jr. | ....... | H04L 41/0823 |

OTHER PUBLICATIONS

Holzman, David C., "What's in a Color? The Unique Human Health Effects of Blue Light," Environmental Health Perspectives, Jan. 2010; 118(1): A22-A27, 6 pages. Retrieved from https://www.ncbi.nlm.nih.gov/pmc/articles/PMC2831986/.

* cited by examiner

*Primary Examiner* — Pankaj Kumar
*Assistant Examiner* — Charles N Hicks
(74) *Attorney, Agent, or Firm* — Kilpatrick Townsend & Stockton LLP

(57) ABSTRACT

In some embodiments, a method, system, or computer-readable storage device including instructions for reducing the blue light component of displayed video can include one or more of the following features: receiving, at a set-top box, a video signal having a white color balance, the white color balance including a red component value. The set-top box can determine that the current time is after a threshold night value and before a threshold morning value and, based on that, adjust the white color balance of the video signal to increase the red component value. The set-top box can then transmit the video signal with the adjusted white color balance to a display device.

20 Claims, 7 Drawing Sheets

REDUCE BLUE LIGHT AT SET-TOP BOX TO ASSIST WITH SLEEP

BACKGROUND OF THE INVENTION

Embodiments of the present application relate generally to methods and systems for managing the color components of a video signal on a television and more particularly to reducing the blue light color component of a video signal displayed on a television through a set-top box to avoid disruption of sleep.

Multiple studies have shown the harmful effects of disrupted circadian rhythms on humans. Issues ranging from depression, diabetes, and even cancer have been linked to desynchronized circadian rhythms. Additional studies have shown that exposure to blue light can be particularly disruptive of circadian rhythms to humans. The disruption can follow even if the blue light exposure occurs during sleep. Further, many people watch television, which includes blue light, in the evening and nighttime hours. As such, systems and methods are needed to reduce the blue light exposure to nighttime television watchers.

BRIEF SUMMARY OF THE INVENTION

In some embodiments, a method, system, or machine-readable storage device including instructions for reducing the blue light component of displayed video can include one or more of the following features: receiving, at a set-top box, a video signal having a white color balance, the white color balance including a red component value. The set-top box can determine that the current time is after a threshold night value and before a threshold morning value and, based on that determination, adjust the white color balance of the video signal to increase the red component value. The set-top box can then transmit the video signal with the adjusted white color balance to a video display device.

In some embodiments, the method, system, or machine-readable storage device can further include one or more of the following features: when the current time reaches a predefined period of time before the threshold night value, gradually adjusting the white color balance of the video signal to increase the red component value incrementally over the predefined period of time. And, when the current time reaches the predefined period of time before the threshold morning value, gradually adjusting the white color balance of the video signal to decrease the red component value incrementally over the predefined period of time. In some embodiments, when the current time reaches the threshold night value, the red component value is a maximum value and a blue component value of the white color balance is a minimum value.

In some embodiments, the method, system, or machine-readable storage device can further include one or more of the following features: providing, by the set-top box, a user interface for configuring one or more parameters. In some embodiments, the parameters can include the threshold night value, the threshold morning value, and/or the predefined period of time. In some embodiments, the white color balance of the video signal after being adjusted to increase the red component value has a blue component value insufficient to disrupt the circadian rhythm of a human.

DETAILED DESCRIPTION OF THE INVENTION

Blue light can be disruptive of circadian rhythms, which can cause trouble sleeping and health issues. This disruption of circadian rhythms can occur at least in part due to evening and/or night time television viewing. The typical television display includes emission of blue light as part of the displayed video, exposing the viewer to blue light. Embodiments of the present invention describe methods and systems for reducing the blue light exposure of television viewers.

Figure 1:
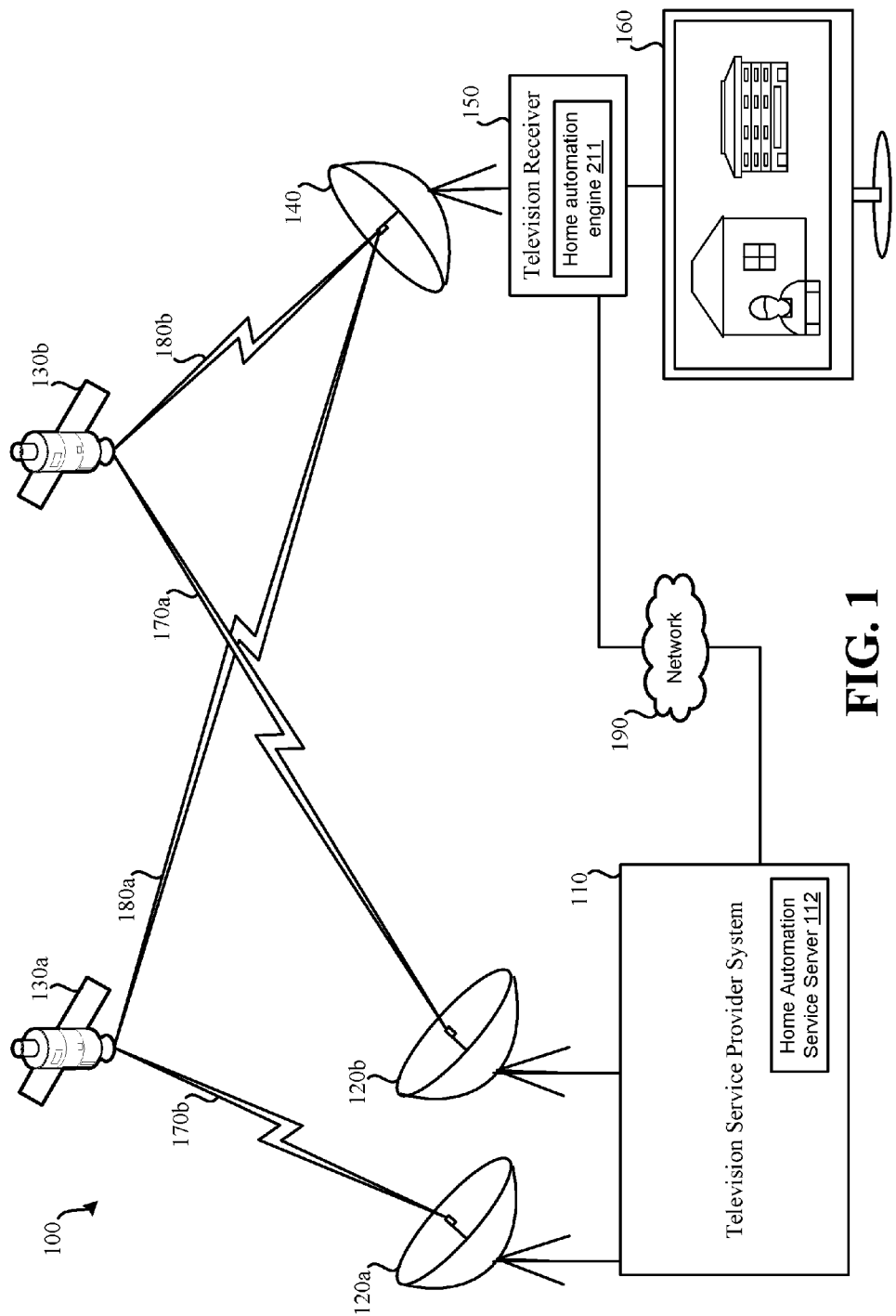
FIG. 1 illustrates an embodiment of a television service provider system that provides home automation functionality.

FIG. 1 illustrates an embodiment of a satellite television distribution system 100. While a home automation system may be incorporated with various types of television receivers, various embodiments may be part of a satellite-based television distribution system. Cable, IP-based, wireless, and broadcast focused systems are also possible. Satellite television distribution system 100 may include: television service provider system 110, satellite transmitter equipment 120, satellites 130, satellite dish 140, television receiver 150, home automation service server 112, and display device 160. The display device 160 can be controlled by, for example, a user using a remote control device that can send wired or wireless signals to communicate with the STB 150 and/or display device 160. Alternate embodiments of satellite television distribution system 100 may include fewer or greater numbers of components. While only one satellite dish 140, television receiver 150, and display device 160 (collectively referred to as "user equipment") are illustrated, it should be understood that multiple (e.g., tens, thousands, millions of) instances and types of user equipment may receive data and television signals from television service provider system 110 via satellites 130.

Television service provider system 110 and satellite transmitter equipment 120 may be operated by a television service provider. A television service provider may distribute television channels, on-demand programming, programming information, and/or other content/services to users. Television service provider system 110 may receive feeds of one or more television channels and content from various sources. Such television channels may include multiple television channels that contain at least some of the same content (e.g., network affiliates). To distribute television channels for presentation to users, feeds of the television channels may be relayed to user equipment via multiple television distribution satellites. Each satellite may relay multiple transponder streams. Satellite transmitter equipment 120 may be used to transmit a feed of one or more television channels from television service provider system 110 to one or more satellites 130. While a single television service provider system 110 and satellite transmitter equipment 120 are illustrated as part of satellite television distribution system 100, it should be understood that multiple instances of transmitter equipment may be used, possibly scattered geographically, to communicate with satellites 130. Such multiple instances of satellite transmitting equipment may communicate with the same or with different satellites. Different television channels may be transmitted to satellites 130 from different instances of transmitting equipment. For instance, a different satellite dish of satellite transmitter equipment 120 may be used for communication with satellites in different orbital slots.

Satellites 130 may be configured to receive signals, such as streams of television channels, from one or more satellite uplinks such as satellite transmitter equipment 120. Satellites 130 may relay received signals from satellite transmitter equipment 120 (and/or other satellite transmitter equipment) to multiple instances of user equipment via transponder streams. Different frequencies may be used for uplink signals 170 from downlink signals 180. Satellites 130 may be in geosynchronous orbit. Each of the transponder streams transmitted by satellites 130 may contain multiple television channels transmitted as packetized data. For example, a single transponder stream may be a serial digital packet stream containing multiple television channels. Therefore, packets for multiple television channels may be interspersed. Further, information used by television receiver 150 for home automation functions may also be relayed to a television receiver via one or more transponder streams.

Multiple satellites 130 may be used to relay television channels from television service provider system 110 to satellite dish 140. Different television channels may be carried using different satellites. Different television channels may also be carried using different transponders of the same satellite; thus, such television channels may be transmitted at different frequencies and/or different frequency ranges. As an example, a first and second television channel may be relayed via a first transponder of satellite 130a. A third, fourth, and fifth television channel may be relayed via a different satellite or a different transponder of the same satellite relaying the transponder stream at a different frequency. A transponder stream transmitted by a particular transponder of a particular satellite may include a finite number of television channels, such as seven. Accordingly, if many television channels are to be made available for viewing and recording, multiple transponder streams may be necessary to transmit all of the television channels to the instances of user equipment.

Satellite dish 140 may be a piece of user equipment that is used to receive transponder streams from one or more satellites, such as satellites 130. Satellite dish 140 may be provided to a subscriber for use on a subscription basis to receive television channels provided by the television service provider system 110, satellite transmitter equipment 120, and/or satellites 130. Satellite dish 140, which may include one or more low noise blocks (LNBs), may be configured to receive transponder streams from multiple satellites and/or multiple transponders of the same satellite. Satellite dish 140 may be configured to receive television channels via transponder streams on multiple frequencies. Based on the characteristics of television receiver 150 and/or satellite dish 140, it may only be possible to capture transponder streams from a limited number of transponders concurrently. For example, a tuner of television receiver 150 may only be able to tune to a single transponder stream from a transponder of a single satellite at a given time. The tuner can then be re-tuned to another transponder of the same or a different satellite. A television receiver 150 having multiple tuners may allow for multiple transponder streams to be received at the same time.

Figure 2:
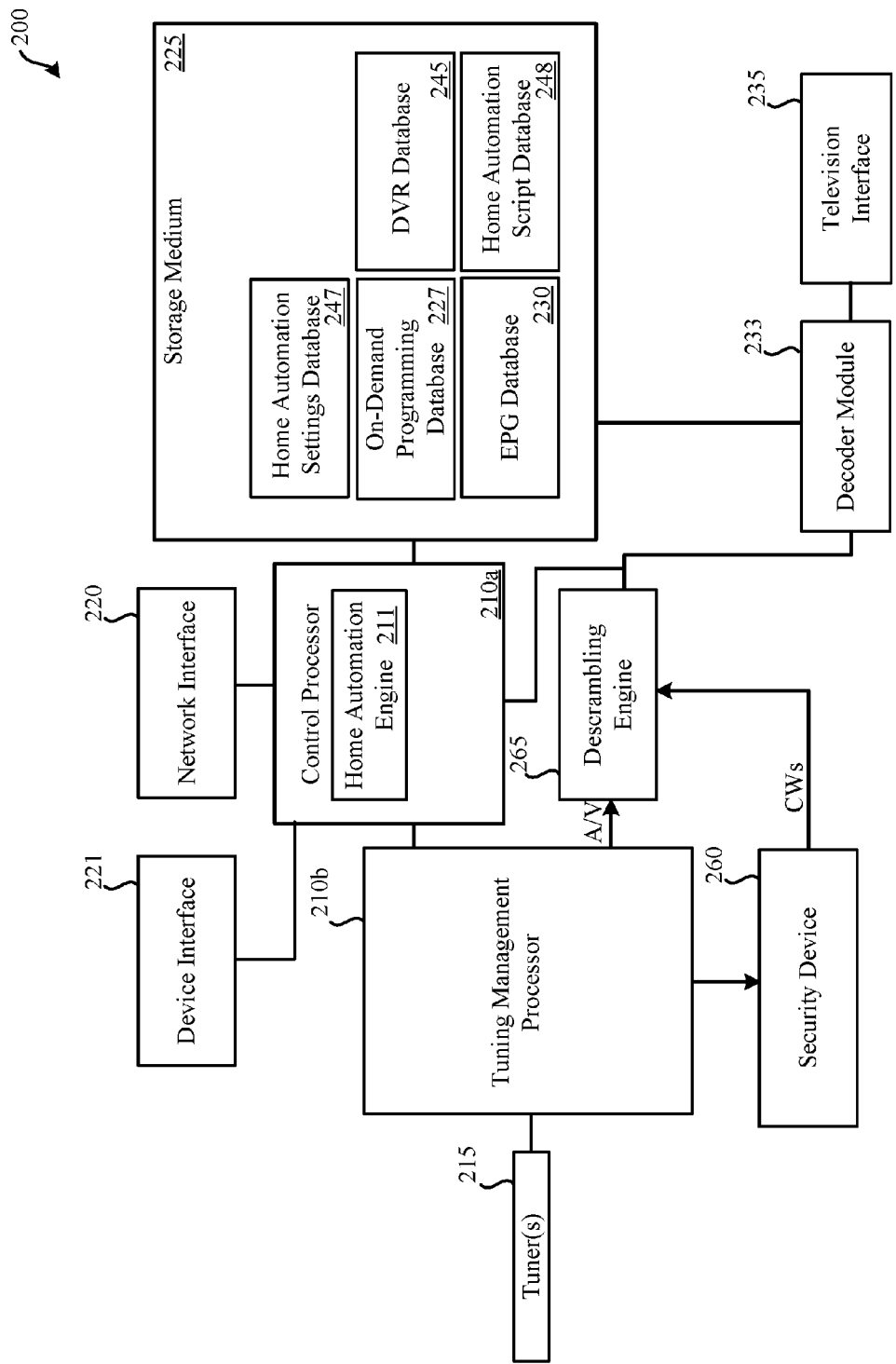
FIG. 2 illustrates an embodiment of a television receiver that functions as a host for a home automation system.

In communication with satellite dish 140 may be one or more television receivers. Television receivers may be configured to decode signals received from satellites 130 via satellite dish 140 for output and presentation via a display device, such as display device 160. A television receiver may be incorporated as part of a television or may be part of a separate device, commonly referred to as a set-top box (STB). Television receiver 150 may decode signals received via satellite dish 140 and provide an output to display device 160. On-demand content, such as PPV content, may be stored to a computer-readable storage medium. FIG. 2 provides additional detail of various embodiments of a television receiver. A television receiver is defined to include set-top boxes (STBs), and also circuitry having similar functionality that may be incorporated with another device. For instance, circuitry similar to that of a television receiver may be incorporated as part of a television. As such, while FIG. 1 illustrates an embodiment of television receiver 150 as separate from display device 160, it should be understood that, in other embodiments, similar functions may be performed by a television receiver integrated with display device 160. Television receiver 150 may include home automation engine 211, as detailed in relation to FIG. 2.

Display device 160 may be used to present video and/or audio decoded and output by television receiver 150. Television receiver 150 may also output a display of one or more interfaces to display device 160, such as an electronic programming guide (EPG). In many embodiments, display device 160 is a television. Display device 160 may also be a monitor, computer, or some other device configured to display video and, possibly, play audio.

Uplink signal 170a represents a signal between satellite transmitter equipment 120 and satellite 130a. Uplink signal 170b represents a signal between satellite transmitter equipment 120 and satellite 130b. Each of uplink signals 170 may contain streams of one or more different television channels. For example, uplink signal 170a may contain a first group of television channels, while uplink signal 170b contains a second group of television channels. Each of these television channels may be scrambled such that unauthorized persons are prevented from accessing the television channels.

Downlink signal 180a represents a signal between satellite 130a and satellite dish 140. Downlink signal 180b represents a signal between satellite 130b and satellite dish 140. Each of downlink signals 180 may contain one or more different television channels, which may be at least partially scrambled. A downlink signal may be in the form of a transponder stream. A single transponder stream may be tuned to at a given time by a tuner of a television receiver. For example, downlink signal 180a may be a first transponder stream containing a first group of television channels, while downlink signal 180b may be a second transponder stream containing a different group of television channels. In addition to or instead of containing television channels, a transponder stream can be used to transmit on-demand content to television receivers, including PPV content, which may be stored locally by the television receiver until output for presentation.

FIG. 1 illustrates downlink signal 180a and downlink signal 180b, being received by satellite dish 140 and distributed to television receiver 150. For a first group of television channels, satellite dish 140 may receive downlink signal 180a and for a second group of channels, downlink signal 180b may be received. Television receiver 150 may decode the received transponder streams. As such, depending on which television channels are desired to be presented or stored, various transponder streams from various satellites may be received, descrambled, and decoded by television receiver 150.

Network 190, which may include the Internet, may allow for bidirectional communication between television receiver 150 and television service provider system 110, such as for home automation related services provided by home automation service server 112. Although illustrated as part of the television service provider system, the home automation service server 112 may be provided by a third party in embodiments. In addition or in alternate to network 190, a telephone, e.g., landline, or cellular connection may be used to enable communication between television receiver 150 and television service provider system 110.

FIG. 2 illustrates an embodiment of a television receiver 200, which may represent television receiver 150 of FIG. 1. Television receiver 200 may be configured to function as a host for a home automation system either alone or in conjunction with a communication device. Television receiver 200 may be in the form of a separate device configured to be connected with a display device, such as a television. Embodiments of television receiver 200 can include set-top boxes (STBs). In addition to being in the form of an STB, a television receiver may be incorporated as part of another device, such as a television, other form of display device, video game console, computer, mobile phone or tablet, or the like. For example, a television may have an integrated television receiver, which does not involve an external STB being coupled with the television.

Television receiver 200 may be incorporated as part of a television, such as display device 160 of FIG. 1. Television receiver 200 may include: processors 210, which may include control processor 210a, tuning management processor 210b, and possibly additional processors, tuners 215, network interface 220, non-transitory computer-readable storage medium 225, electronic programming guide (EPG) database 230, television interface 235, digital video recorder (DVR) database 245, which may include provider-managed television programming storage and/or user-defined television programming, on-demand programming database 227, home automation settings database 247, home automation script database 248, remote control interface 250, security device 260, and/or descrambling engine 265. In other embodiments of television receiver 200, fewer or greater numbers of components may be present. It should be understood that the various components of television receiver 200 may be implemented using hardware, firmware, software, and/or some combination thereof. Functionality of components may be combined; for example, functions of descrambling engine 265 may be performed by tuning management processor 210b. Further, functionality of components may be spread among additional components.

Processors 210 may include one or more specialized and/or general-purpose processors configured to perform processes such as tuning to a particular channel, accessing and displaying EPG information from EPG database 230, and/or receiving and processing input from a user. It should be understood that the functions performed by various modules of FIG. 2 may be performed using one or more processors. As such, for example, functions of descrambling engine 265 may be performed by control processor 210a.

Control processor 210a may communicate with tuning management processor 210b. Control processor 210a may control the recording of television channels based on timers stored in DVR database 245. Control processor 210a may also provide commands to tuning management processor 210b when recording of a television channel is to cease. In addition to providing commands relating to the recording of television channels, control processor 210a may provide commands to tuning management processor 210b that indicate television channels to be output to decoder module 233 for output to a display device. Control processor 210a may also communicate with network interface 220 and remote control interface 250. Control processor 210a may handle incoming data from network interface 220 and remote control interface 250. Additionally, control processor 210a may be configured to output data via network interface 220.

Control processor 210a may include home automation engine 211. Home automation engine 211 may permit television receiver and control processor 210a to provide home automation functionality. Home automation engine 211 may have a JSON (JavaScript Object Notation) command interpreter or some other form of command interpreter that is configured to communicate with wireless devices via network interface 220 and a message server, possibly via a message server client. Such a command interpreter of home automation engine 211 may also communicate via a local area network with devices without using the Internet. Home automation engine 211 may contain multiple controllers specific to different protocols; for instance, a ZigBee® controller, a Z-Wave® controller, and/or an IP camera controller, wireless LAN, 802.11, may be present. Home automation engine 211 may contain a media server configured to serve streaming audio and/or video to remote devices on a local area network or the Internet. Television receiver may be able to serve such devices with recorded content, live content, and/or content recorded using one or more home automation devices, such as cameras.

Tuners 215 may include one or more tuners used to tune to transponders that include broadcasts of one or more television channels. Such tuners may be used also to receive for storage on-demand content and/or addressable television commercials. In some embodiments, two, three, or more than three tuners may be present, such as four, six, or eight tuners. Each tuner contained in tuners 215 may be capable of receiving and processing a single transponder stream from a satellite transponder or from a cable network at a given time. As such, a single tuner may tune to a single transponder stream at a given time. If tuners 215 include multiple tuners, one tuner may be used to tune to a television channel on a first transponder stream for display using a television, while another tuner may be used to tune to a television channel on a second transponder for recording and viewing at some other time. If multiple television channels transmitted on the same transponder stream are desired, a single tuner of tuners 215 may be used to receive the signal containing the multiple television channels for presentation and/or recording. Tuners 215 may receive commands from tuning management processor 210b. Such commands may instruct tuners 215 to which frequencies are to be tuned.

Network interface 220 may be used to communicate via an alternate communication channel with a television service provider, if such communication channel is available. A communication channel may be via satellite, which may be unidirectional to television receiver 200, and the alternate communication channel, which may be bidirectional, may be via a network, such as the Internet. Data may be transmitted from television receiver 200 to a television service provider system and from the television service provider system to television receiver 200. Information may be transmitted and/or received via network interface 220. For instance, instructions from a television service provider may also be received via network interface 220, if connected with the Internet. Besides the primary communication channel being satellite, cable network, an IP-based network, or broadcast network may be used. Network interface 220 may permit wireless communication with one or more types of networks, including using home automation network protocols and wireless network protocols. Also, wired networks may be connected to and communicated with via network interface 220. Device interface 221 may represent a USB port or some other form of communication port that permits communication with a communication device as will be explained further below.

Storage medium 225 may represent one or more non-transitory computer-readable storage mediums. Storage medium 225 may include memory and/or a hard drive. Storage medium 225 may be used to store information received from one or more satellites and/or information received via network interface 220. Storage medium 225 may store information related to on-demand programming database 227, EPG database 230, DVR database 245, home automation settings database 247, and/or home automation script database 248. Recorded television programs may be stored using storage medium 225 as part of DVR database 245. Storage medium 225 may be partitioned or otherwise divided, such as into folders, such that predefined amounts of storage medium 225 are devoted to storage of television programs recorded due to user-defined timers and stored television programs recorded due to provider-defined timers.

Home automation settings database 247 may allow configuration settings of home automation devices and user preferences to be stored. Home automation settings database 247 may store data related to various devices that have been set up to communicate with television receiver 200. For instance, home automation settings database 247 may be configured to store information on which types of events should be indicated to users, to which users, in what order, and what communication methods should be used. For instance, an event such as an open garage may only be notified to certain wireless devices, e.g., a cellular phone associated with a parent, not a child, notification may be by a third-party notification server, email, text message, and/or phone call. In some embodiments, a second notification method may only be used if a first fails. For instance, if a notification cannot be sent to the user via a third-party notification server, an email may be sent.

Home automation settings database 247 may store information that allows for the configuration and control of individual home automation devices which may operate using Z-wave® and ZigBee®-specific protocols. To do so, home automation engine 211 may create a proxy for each device that allows for settings for the device to be passed through a UI, e.g., presented on a television, to allow for settings to be solicited for and collected via a user interface presented by television receiver or overlay device. The received settings may then be handled by the proxy specific to the protocol, allowing for the settings to be passed on to the appropriate device. Such an arrangement may allow for settings to be collected and received via a UI of the television receiver or overlay device and passed to the appropriate home automation device and/or used for managing the appropriate home automation device. For example, a piece of exercise equipment that is enabled to interface with the home automation engine 211, such as via device interface 221, may be configured at the electronic device 211 in addition to on the piece of exercise equipment itself. Additionally, a mobile device or application residing on a mobile device and utilized with exercise equipment may be configured in such a fashion as well for displaying received fitness information on a coupled display device.

Home automation script database 248 may store scripts that detail how home automation devices are to function based on various events occurring. For instance, if stored content starts being played back by television receiver 200, lights in the vicinity of display device 160 may be dimmed and shades may be lowered by communicatively coupled and controlled shade controller. As another example, when a user shuts programming off late in the evening, there may be an assumption the user is going to bed. Therefore, the user may configure television receiver 200 to lock all doors via a lock controller, shut the garage door via garage controller, lower a heat setting of thermostat, shut off all lights via a light controller, and determine if any windows or doors are open via window sensors and door sensors, and, if so, alert the user. Such scripts or programs may be predefined by the home automation/television service provider and/or may be defined by a user.

In some embodiments, home automation script database 248 may allow for various music profiles to be implemented. For instance, based on home automation settings within a structure, appropriate music may be played. For instance, when a piece of exercise equipment is connected or is used, energizing music may be played. Conversely, based on the music being played, settings of home automation devices may be determined. If television programming, such as a movie, is output for playback by television receiver 150, a particular home automation script may be used to adjust home automation settings, e.g., lower lights, raise temperature, and lock doors.

EPG database 230 may store information related to television channels and the timing of programs appearing on such television channels. EPG database 230 may be stored using storage medium 225, which may be a hard drive or solid-state drive. Information from EPG database 230 may be used to inform users of what television channels or programs are popular and/or provide recommendations to the user. Information from EPG database 230 may provide the user with a visual interface displayed by a television that allows a user to browse and select television channels and/or television programs for viewing and/or recording. Information used to populate EPG database 230 may be received via network interface 220, via satellite, or some other communication link with a television service provider, e.g., a cable network. Updates to EPG database 230 may be received periodically. EPG database 230 may serve as an interface for a user to control DVR functions of television receiver 200, and/or to enable viewing and/or recording of multiple television channels simultaneously. EPG database 240 may also contain information about on-demand content or any other form of accessible content.

Decoder module 233 may serve to convert encoded video and audio into a format suitable for output to a display device. For instance, decoder module 233 may receive MPEG video and audio from storage medium 225 or descrambling engine 265 to be output to a television. MPEG video and audio from storage medium 225 may have been recorded to DVR database 245 as part of a previously-recorded television program. Decoder module 233 may convert the MPEG video and audio into a format appropriate to be displayed by a television or other form of display device and audio into a format appropriate to be output from speakers, respectively. Decoder module 233 may have the ability to convert a finite number of television channel streams received from storage medium 225 or descrambling engine 265, simultaneously. For instance, decoders within decoder module 233 may be able to only decode a single television channel at a time. Decoder module 233 may have various numbers of decoders.

Television interface 235 may serve to output a signal to a television or another form of display device in a proper format for display of video and playback of audio. As such, television interface 235 may output one or more television channels, stored television programming from storage medium 225, e.g., television programs from DVR database 245, television programs from on-demand programming 230 and/or information from EPG database 230, to a television for presentation. Television interface 235 may also serve to output a CVM.

Digital Video Recorder (DVR) functionality may permit a television channel to be recorded for a period of time. DVR functionality of television receiver 200 may be managed by control processor 210a. Control processor 210a may coordinate the television channel, start time, and stop time of when recording of a television channel is to occur. DVR database 245 may store information related to the recording of television channels. DVR database 245 may store timers that are used by control processor 210a to determine when a television channel should be tuned to and its programs recorded to DVR database 245 of storage medium 225. In some embodiments, a limited amount of storage medium 225 may be devoted to DVR database 245. Timers may be set by the television service provider and/or one or more users of television receiver 200.

DVR database 245 may also be used to record recordings of service provider-defined television channels. For each day, an array of files may be created. For example, based on provider-defined timers, a file may be created for each recorded television channel for a day. For example, if four television channels are recorded from 6-10 PM on a given day, four files may be created; one for each television channel. Within each file, one or more television programs may be present. The service provider may define the television channels, the dates, and the time periods for which the television channels are recorded for the provider-defined timers. The provider-defined timers may be transmitted to television receiver 200 via the television provider's network. For example, in a satellite-based television service provider system, data necessary to create the provider-defined timers at television receiver 150 may be received via satellite.

On-demand programming database 227 may store additional television programming. On-demand programming database 227 may include television programming that was not recorded to storage medium 225 via a timer, either user- or provider-defined. Rather, on-demand programming may be programming provided to the television receiver directly for storage by the television receiver and for later presentation to one or more users. On-demand programming may not be user-selected. As such, the television programming stored to on-demand programming database 227 may be the same for each television receiver of a television service provider. On-demand programming database 227 may include pay-per-view (PPV) programming that a user must pay and/or use an amount of credits to view. For instance, on-demand programming database 227 may include movies that are not available for purchase or rental yet.

Referring back to tuners 215, television channels received via satellite or cable may contain at least some scrambled data. Packets of audio and video may be scrambled to prevent unauthorized users, e.g., nonsubscribers, from receiving television programming without paying the television service provider. When a tuner of tuners 215 is receiving data from a particular transponder of a satellite, the transponder stream may be a series of data packets corresponding to multiple television channels. Each data packet may contain a packet identifier (PID), which can be determined to be associated with a particular television channel. Particular data packets, referred to as entitlement control messages (ECMs), may be periodically transmitted. ECMs may be associated with another PID and may be encrypted; television receiver 200 may use decryption engine 261 of security device 260 to decrypt ECMs. Decryption of an ECM may only be possible if the user has authorization to access the particular television channel associated with the ECM. When an ECM is determined to correspond to a television channel being stored and/or displayed, the ECM may be provided to security device 260 for decryption.

When security device 260 receives an encrypted ECM, security device 260 may decrypt the ECM to obtain some number of control words. In some embodiments, from each ECM received by security device 260, two control words are obtained. In some embodiments, when security device 260 receives an ECM, it compares the ECM to the previously received ECM. If the two ECMs match, the second ECM is not decrypted because the same control words would be obtained. In other embodiments, each ECM received by security device 260 is decrypted; however, if a second ECM matches a first ECM, the outputted control words will match; thus, effectively, the second ECM does not affect the control words output by security device 260. Security device 260 may be permanently part of television receiver 200 or may be configured to be inserted and removed from television receiver 200, such as a smart card, cable card, or the like.

Tuning management processor 210b may be in communication with tuners 215 and control processor 210a. Tuning management processor 210b may be configured to receive commands from control processor 210a. Such commands may indicate when to start/stop receiving and/or recording of a television channel and/or when to start/stop causing a television channel to be output to a television. Tuning management processor 210b may control tuners 215. Tuning management processor 210b may provide commands to tuners 215 that instruct the tuners which satellite, transponder, and/or frequency to tune to. From tuners 215, tuning management processor 210b may receive transponder streams of packetized data.

Descrambling engine 265 may use the control words output by security device 260 in order to descramble video and/or audio corresponding to television channels for storage and/or presentation. Video and/or audio data contained in the transponder data stream received by tuners 215 may be scrambled. Video and/or audio data may be descrambled by descrambling engine 265 using a particular control word. Which control word output by security device 260 to be used for successful descrambling may be indicated by a scramble control identifier present within the data packet containing the scrambled video or audio. Descrambled video and/or audio may be output by descrambling engine 265 to storage medium 225 for storage, in DVR database 245, and/or to decoder module 233 for output to a television or other presentation equipment via television interface 235.

In some embodiments, the television receiver 200 may be configured to periodically reboot in order to install software updates downloaded over the network 190 or satellites 130. Such reboots may occur for example during the night when the users are likely asleep and not watching television. If the system utilizes a single processing module to provide television receiving and home automation functionality, then the security functions may be temporarily deactivated. In order to increase the security of the system, the television receiver 200 may be configured to reboot at random times during the night in order to allow for installation of updates. Thus, an intruder is less likely to guess the time when the system is rebooting. In some embodiments, the television receiver 200 may include multiple processing modules for providing different functionality, such as television receiving functionality and home automation, such that an update to one module does not necessitate reboot of the whole system. In other embodiments, multiple processing modules may be made available as a primary and a backup during any installation or update procedures.

For simplicity, television receiver 200 of FIG. 2 has been reduced to a block diagram; commonly known parts, such as a power supply, have been omitted. Further, some routing between the various modules of television receiver 200 has been illustrated. Such illustrations are for exemplary purposes only. The state of two modules not being directly or indirectly connected does not indicate the modules cannot communicate. Rather, connections between modules of the television receiver 200 are intended only to indicate possible common data routing. It should be understood that the modules of television receiver 200 may be combined into a fewer number of modules or divided into a greater number of modules. Further, the components of television receiver 200 may be part of another device, such as built into a television. Television receiver 200 may include one or more instances of various computerized components, such as disclosed in relation to computer system 700 of FIG. 7.

While the television receiver 200 has been illustrated as a satellite-based television receiver, it is to be appreciated that techniques below may be implemented in other types of television receiving devices, such a cable receivers, terrestrial receivers, IPTV receivers or the like. In some embodiments, the television receiver 200 may be configured as a hybrid receiving device, capable of receiving content from disparate communication networks, such as satellite and terrestrial television broadcasts. In some embodiments, the tuners may be in the form of network interfaces capable of receiving content from designated network locations. The home automation functions of television receiver 200 may be performed by an overlay device. If such an overlay device is used, television programming functions may still be provided by a television receiver that is not used to provide home automation functions.

Figure 3:
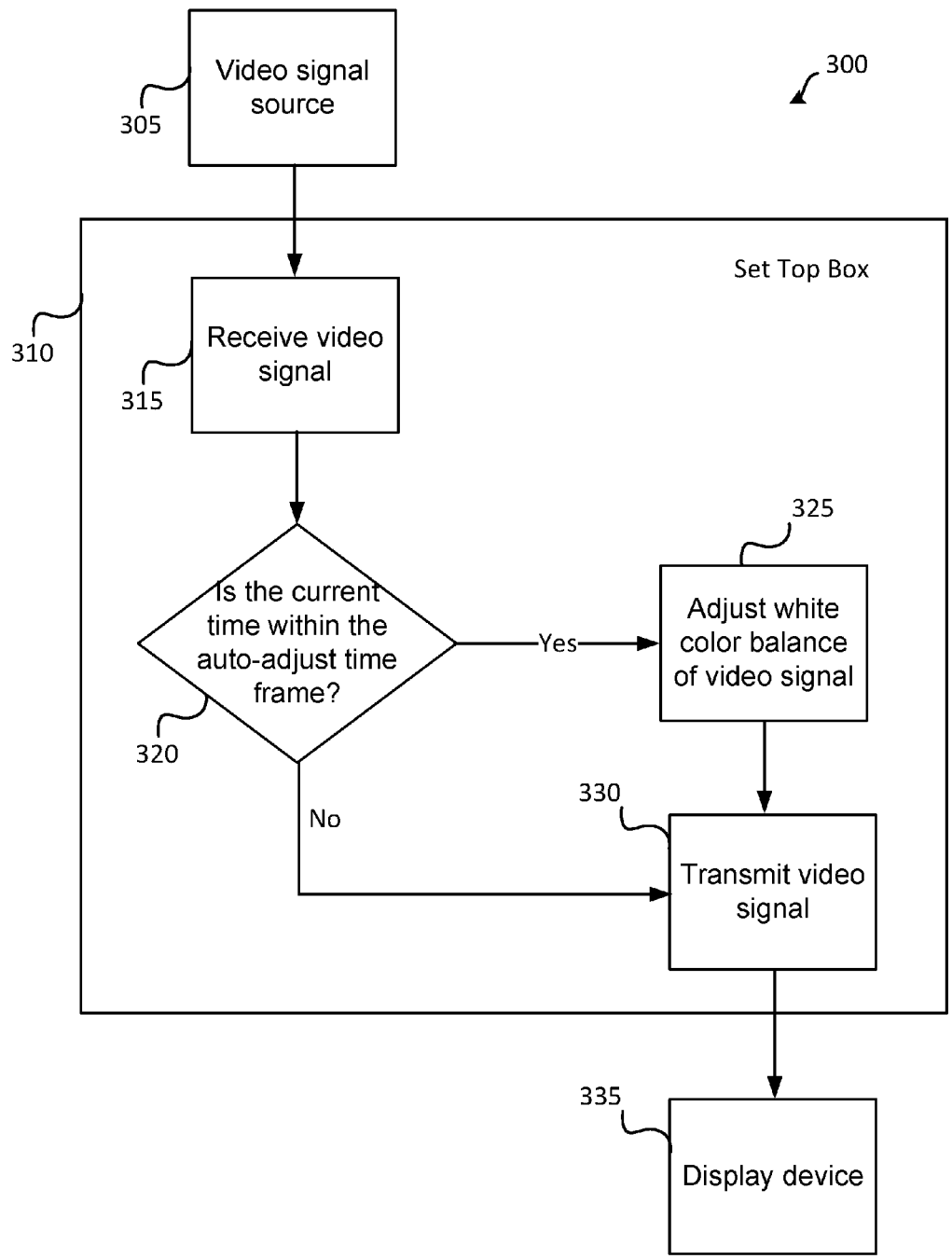
FIG. 3 illustrates a simplified block diagram of a system for reducing blue light in a set-top box.

FIG. 3 illustrates a simplified block diagram of a system 300 for reducing blue light in a set-top box. The system 300 can include a video signal source 305, a set-top box 310, and a display device 335. The set-top box 310 can include modules for receiving the video signal 315, determining whether the time is within the time frame for auto-adjusting the time frame 320, adjusting the white color balance of the video signal 325, and transmitting the video signal 330.

Video signal source 305 can be any video signal source that transmits video signals to a television receiver or set-top box. For example, video signal source 305 can be the television service provider 110 as described with respect to FIG. 1. As described in FIG. 1, the transmitter equipment 120, satellite 130, and satellite dish 140 can relay the video signal from the television service provider to the television receiver. In some embodiments, the video signal can be previously stored in the set-top box 310. For example, the video signal can be stored in DVR database 245 or on-demand programming database 227 as described with respect to FIG. 2.

The set-top box 310 can be the television receiver 150 as described with respect to FIG. 1 or the television receiver 200 as described with respect to FIG. 2. The set-top box 310 can include, in addition to those described with respect to FIG. 2, modules or other programming components that adjust the blue light of the received video signal. In some embodiments, the components that adjust the blue light of the received video signal can be included in decoder module 233 as described with respect to FIG. 2 or can be additional components or modules implemented after the video signal is decoded by decoder module 233. While described as modules for performing the individually described functions for adjusting the blue light of the received video signal, it should be understood that the modules can be grouped together or differently than described. Instructions for completing the functions can be stored on, for example, a storage medium such as storage medium 225 of FIG. 2.

The set-top box 310 can receive the video signal 315 as described, for example, with respect to FIG. 2. Once the set-top box 310 has received the video signal, the set-top box 310 can determine whether the current time is within the auto-adjust time frame 320. For example, the auto-adjust time frame can be 7:00 p.m. until 6:00 a.m. If the current time is 8:00 p.m., the current time falls within the auto-adjust time frame. If the current time is 4:00 p.m., the current time does not fall within the auto-adjust time frame. The set-top box 310 can know the current time because, for example, it has a clock that has been set or, as another example, it receives the current time from the television service provider.

The auto-adjust time frame can be set automatically as a feature of the set-top box 310. In some embodiments, the auto-adjust time frame can be set to reduce blue light so that television viewing is least disruptive to circadian rhythms (e.g., the blue light reduction occurs early enough in the evening and lasts late enough in the morning to cause the least circadian rhythm disruption). In some embodiments, the auto-adjust time frame can be configured, for example, through a user interface displayed on display device 335. The user interface can allow a user to configure various parameters of the described features of the set-top box 310 for reducing blue light. For example, in some embodiments, a user can set the auto-adjust time frame (i.e., the threshold night value and the threshold morning value), the amount of reduction of the blue light, and a time duration for gradually adjusting the blue light. In some embodiments, the auto-adjust features can have default settings that are configurable by a user.

If the set-top box 310 determines that the current time is not within the auto-adjust time frame, the set-top box 310 can simply transmit or output the video signal at 330. The transmission or output of the video signal to the display device 335 can be as described, for example, via television interface 235 with respect to FIG. 2. If the set-top box 310 determines that the current time is within the auto-adjust time frame, the set-top box 310 can adjust the white color balance of the video signal at 325.

Images and video include a white color balance. Color on a television or other display device screen is typically a combination of red, green, and blue (RGB) components or light. In some embodiments, the color model used can be CMYK rather than RGB. An RGB color model is a color model that uses red (R), green (G), and blue (B) (collectively "RGB"). A CMYK color model is a color model that uses cyan (C), magenta (M), yellow (Y), and black (K) (collectively "CMYK"). While described throughout as utilizing an RGB color model, the same techniques can be applied to other color models, such as CMYK.

Typically, an equal combination of the three colors (red, green, and blue), results in a white display. However, the white color balance can be adjusted to account for various lighting differences in the capture of the video or the desired display of the video. When the white color balance is adjusted, a correction is made to the balance of colors (e.g., red, green, and blue) so that what should appear white is actually white. Additionally, the white color balance can also be adjusted to make what should be white instead appear to be more reddish, bluish, or greenish. For example, if white should include 33.3% red, 33.3% green, and 33.3% blue, the color white on a screen can be shifted toward red by adjusting the white color balance to include 50% red, 33.3% green, and 16.7% blue. Consequently, other colors will also be shifted toward red because the white color balance can be the baseline for all color adjustments on a display device. Stated differently, the white color balance of an image affects all colors displayed in the image—not only white. Because all colors are affected by the white color balance, if the white color balance is shifted toward red and away from blue, for example, all colors on the screen will appear more reddish and less bluish. Similarly, the white color balance can be shifted toward green or blue by making adjustments to increase the percentage of green or blue, respectively. It should be noted that while described as percentages here, in some embodiments, the components of each color of the RGB color model can be expressed in other ways, such as, for example, an integer number in the range of 0 to 255.

The set-top box 310 can adjust the white color balance of the video signal at 325 to reduce the blue light by, for example, shifting the white color balance toward red. The automatic adjustment of the white color balance can be done gradually or instantly. By adjusting the white color balance instantly, the viewer can more easily notice the change. In some embodiments, a change to the white color balance can be done gradually to make the adjustment less noticeable to the viewer.

In some embodiments, the amount of the white color balance shift can be modified, for example, though a user interface. The user can, for example, set the white color balance to be optimized for reduction or elimination of circadian rhythm disruption (i.e., the blue component value is insufficient to disrupt the circadian rhythm of a human). In some embodiments, the white color balance can be set to decrease the blue light component to a minimum (e.g., 0%) and increase the red light component to a maximum (e.g., 66.6%).

Once the white color balance of the video signal has been adjusted, if needed, the video signal can be transmitted or output at 330 to a display device 335. Display device 335 can be, for example, display device 160 as described with respect to FIG. 1. The adjusted video signal can be output or transmitted at 330 using, for example, television interface 235 as described with respect to FIG. 2.

Figure 4:
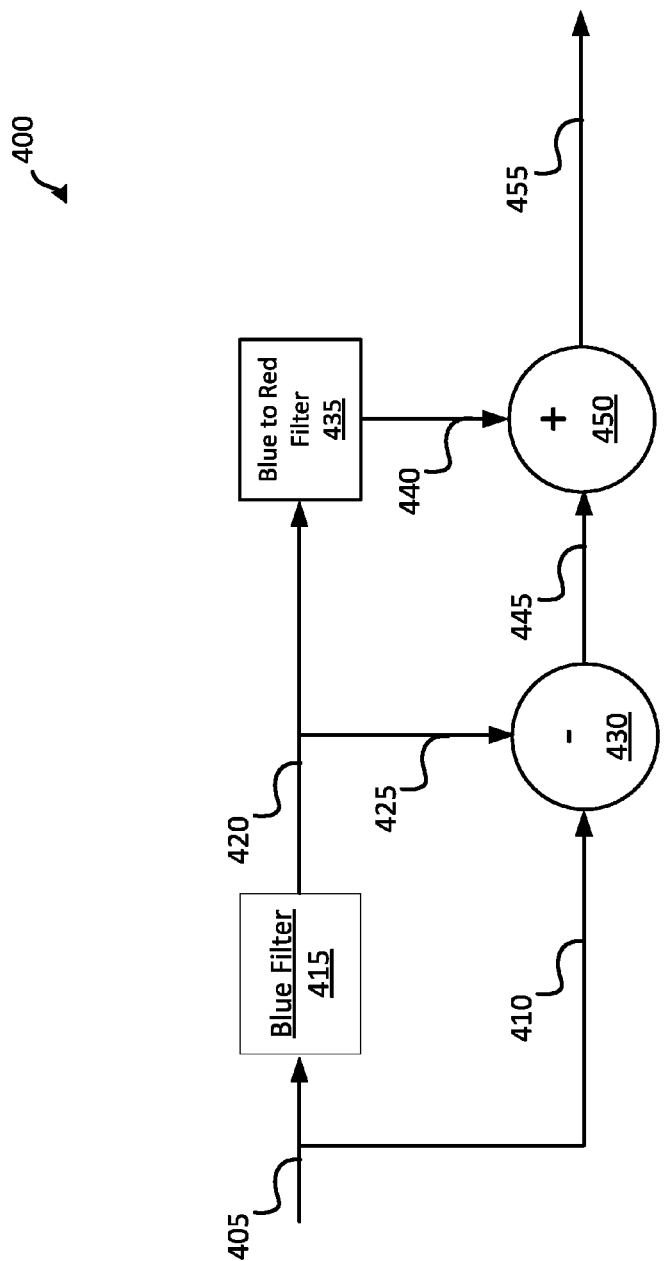
FIG. 4 illustrates another block diagram of a system for reducing blue light in a set-top box.

FIG. 4 illustrates another block diagram of a system 400 for reducing blue light in a set-top box. The system 400 described in FIG. 4 can be used to adjust the white color balance of the video signal 325 as described with respect to FIG. 3. The system 400 can include a blue filter 415, a blue to red filter 435, a subtraction block 430, and an addition block 450.

The video signal 405 can enter the system 400 for reducing blue light. The video signal 405 can be a complete video signal as intended for viewing, such as that received by tuners 215 and processed by decoder module 233 and/or stored in DVR database 245 or on-demand programming database 227 as described with respect to FIG. 2. The video signal 405 can enter blue filter 415. Blue filter 415 can filter the video signal 405, leaving only the blue portion of the video signal, which emerges from the filter as video signal 420. In some embodiments, the blue filter can filter some portion or all of the blue component of the video signal 405. The amount of the blue filter can be configured by, for example, a user interface. In some embodiments, the video signal 405 can be gradually filtered over a predetermined period of time such that over the predetermined period of time the filtering increases gradually until it reaches the complete desired filter. A viewer is less likely to notice, be confused by, or be annoyed by such gradual filtering.

The video signal 410 can branch off from video signal 405. Video signal 410 can be a duplicate of video signal 405—a complete video signal as intended for viewing. Video signal 410 can enter subtraction module 430. Video signal 425 can branch off of video signal 420, being a duplicate, containing some or all of the blue portion of the video signal that emerged from blue filter 415. Video signal 425 can enter subtraction module 430. Subtraction module 430 can subtract the blue portion of the video signal 425 from original video signal 410 resulting in a video signal with a reduced blue component 445.

Video signal 420 can enter blue to red filter 435. Blue to red filter 435 can adjust the video signal 420 from blue to red. Video signal 440 that can emerge from blue to red filter 435 can be the portion of the video signal 405 that was originally blue but has been adjusted to red.

Video signal 440 can enter addition module 450 and video signal 445 can also enter addition module 450. Video signal 445 can be the portion of the video signal 405 that remains after at least some of the blue portion of the video signal has been removed. Video signal 440 is the blue portion of the original video signal 405 after it has been adjusted to red. Addition module 450 can add the video signal 445 to video signal 440, resulting in video signal 455, which can be the full video signal with the blue portion of the video signal adjusted to red.

Figure 5:
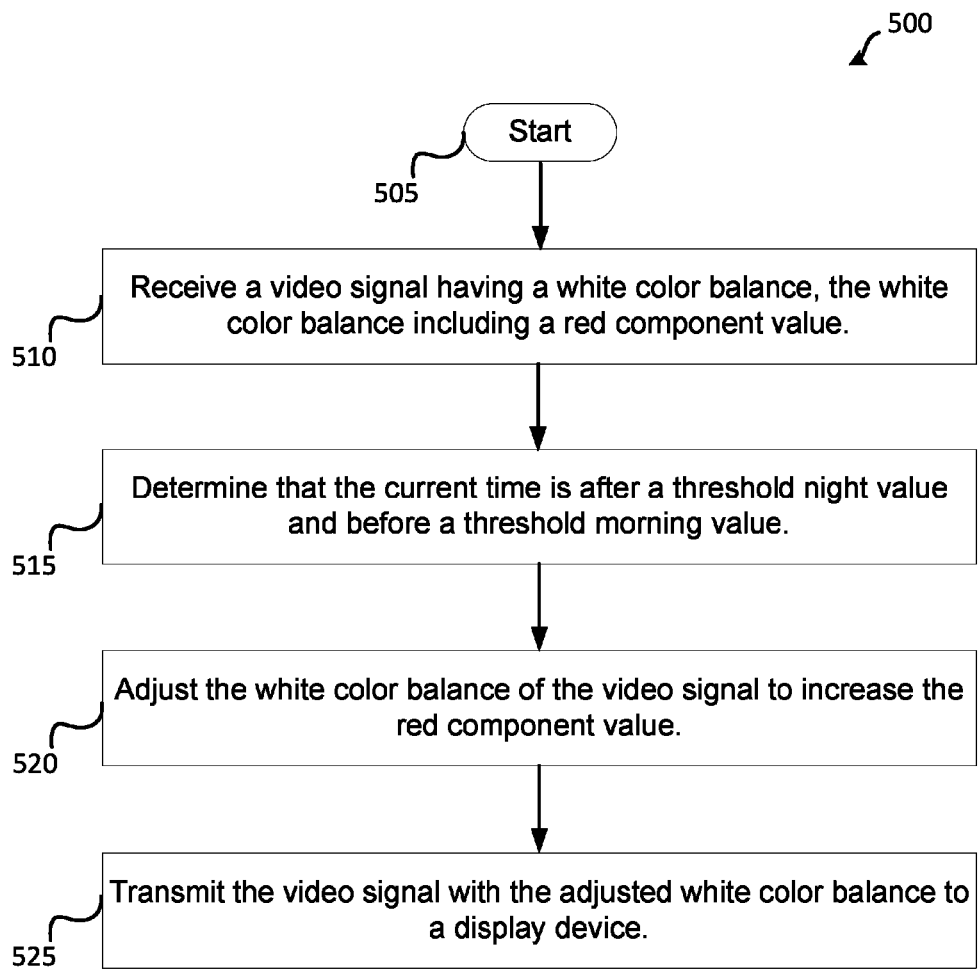
FIG. 5 illustrates a method for reducing blue light in a set-top box.

FIG. 5 illustrates a method 500 for reducing blue light in a set-top box that begins at 505. The method 500 can be performed by a set-top box, such as set-top box 200 as described with respect to FIG. 2.

At 510, the set-top box can receive a video signal having a white color balance. The white color balance can be set such that white colors are displayed by a color mix that is substantially equal (e.g., red 33.3%, green 33.3%, and blue 33.3%). The white color balance in the video signal can include a red component and a blue component. As previously noted, the color model can be RGB, CMYK, or any other suitable color model.

At 515, the set-top box can determine that the current time is after a threshold night value and before a threshold morning value. Stated another way, the set-top box can determine that the current time is within an auto-adjust time frame. As an example, the threshold night value can be set to 8 p.m. and the threshold morning value can be set to 8 a.m. In that example, when the current time falls after 8 p.m. and before 8 a.m., the current time is within the auto-adjust time frame (i.e., after the threshold night value and before the threshold morning value). In some embodiments, the threshold morning and night values can be automatically pre-configured within the set-top box to a default value when the blue light reduction functionality is installed on the set-top box. In some embodiments, the threshold morning and night values can be configured by a user via, for example, a user interface that can be displayed through a display device, such as, for example, a television.

At 520, the set-top box can adjust the white color balance of the video signal to increase the red component value. As described with respect to FIGS. 3 and 4, the set-top box can adjust the white color balance of the video signal by reducing the blue component and increasing the red component. In some embodiments, the blue light can be reduced by adjusting the white color balance in any way such that the result is that the blue component is reduced, including increasing the red or the green component. In some embodiments using a different color model, for example a CMYK color model, the white color balance of the video signal can be adjusted in any suitable way to reduce the blue light component of the video signal. In some embodiments, the video signal can be reprocessed to reduce the blue light. In other embodiments, the carrier signal of the video can include information that modifies the displayed color. In other embodiments, the set-top box can transmit a signal with the video signal that causes the television to modify the color display, shifting the white color balance of the display.

At 525, the set-top box can transmit or output the video signal with the adjusted white color balance to a display device. The display device can be, for example, display device 160 as described with respect to FIG. 1. The video signal can be transmitted or output using television interface 235 as described with respect to FIG. 2.

Figure 6:
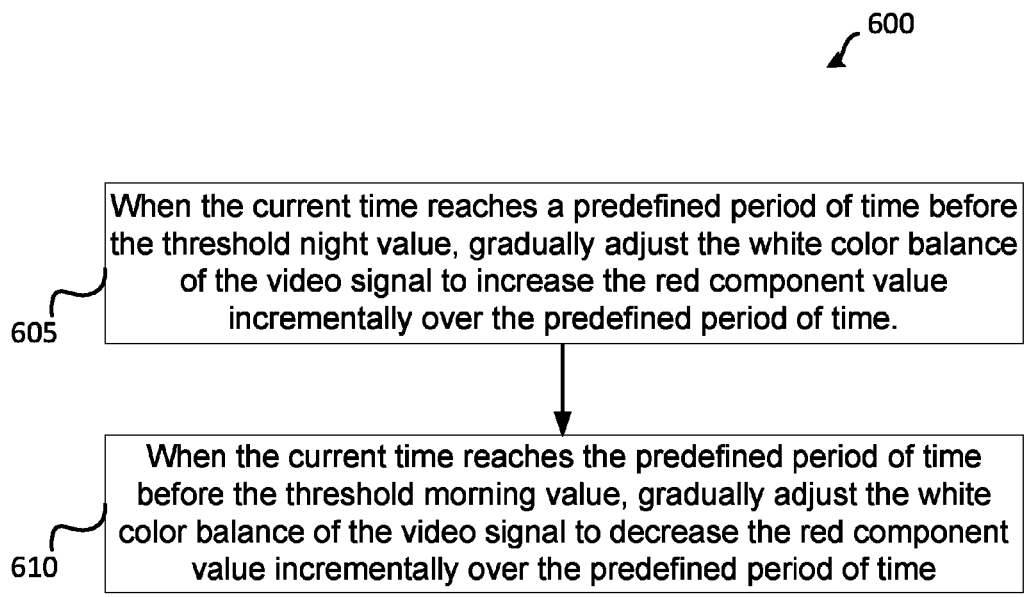
FIG. 6 illustrates another method for reducing blue light in a set-top box.

FIG. 6 illustrates a method 600 for reducing blue light in a set-top box. Method 600 can be used in addition to method 500 of FIG. 5. The method 600 can be performed by a set-top box, such as set-top box 200 as described with respect to FIG. 2. At 605, when the current time reaches a predefined period of time before the threshold night value, the set-top box can gradually adjust the white color balance of the video signal to increase the red component value incrementally over the predefined period of time. Method 600 can be implemented to reduce the obviousness of the change for the viewer.

For example, if a viewer is watching television at 7:30 p.m., and the threshold night value is set for 8:00 p.m., at 8:00 p.m., the video would suddenly change to remove or reduce the blue light component of the video. This change could be noticeable, confusing, and/or annoying to the viewer if it happens suddenly. Method 600 can allow for configuration of a predefined period of time over which to gradually reduce the blue light component of the video. The predefined period of time can be set to a default when the blue light reduction functionality is implemented on the set-top box. In some embodiments, the predefined period of time can be turned on or off or configurable by the user in the user interface available via the display device. For example, the user can, in some embodiments, configure the predefined period of time length. The default setting can be, for example, five minutes, and the user can configure the predefined period of time to be greater or less than five minutes. If the predefined period of time is configured to be five minutes and the threshold night value is 8:00 p.m., at 7:55 p.m., the amount of the red light component in the video signal can increase, for example, from 33.3% to 50% gradually over the five minute interval. Correspondingly, the amount of the blue light component in the video signal can decrease, for example, from 33.3% to 16.7% gradually over the five minute interval. In some embodiments, the predefined period of time to gradually increase the red light component of the video signal can begin at the threshold night value and the gradual change can be complete the predetermined period of time after the threshold night value (e.g., the gradual change can begin at 8:00 p.m. and be complete at 8:05 p.m. if the threshold night value is 8:00 p.m. and the predetermined period of time is five minutes).

Similarly, when the morning threshold value is reached, the reversion back to standard video without the adjustment can be noticeable, confusing, and/or annoying to the viewer. At 610, when the current time reaches a predefined period of time before the threshold morning value, the set-top box can gradually adjust the white color balance of the video signal to decrease the red component value incrementally over the predefined period of time. The predefined period of time before the threshold morning value can be the same as the predefined period of time before the night threshold value (e.g., both are five minutes) or it can be different (e.g., night can be 5 minutes and morning can be 2 minutes). As an example, if the threshold morning value is 6:00 a.m. and the predefined period of time is five minutes, at 5:55 a.m., the amount of red light increase can be gradually decreased, for example, from 50% to 33.3% gradually over the five minute interval. Correspondingly, the amount of blue light reduction in the video signal can decrease gradually, for example, from 16.7% to 33.3% over the five minute interval. In some embodiments, the gradual decrease can occur over the predetermined period of time once the morning threshold value has been reached (e.g., the gradual change can begin at 6:00 a.m. and be complete at 6:05 a.m. if the threshold morning value is 6:00 a.m. and the predetermined period of time is five minutes).

In some embodiments, the increase and decrease can be done, for example using the blue filter 415 as described with respect to FIG. 4, such that the blue filter 415 filters only some of the blue portion of the video signal, which can be gradually modified to filter more or less of the signal. For example, as the current time proceeds closer to the night threshold value, the amount that the blue filter 415 filters increases. Similarly, as the current time proceeds closer to the morning threshold value, the amount that the blue filter 415 filters decreases.

In some embodiments, the viewer can turn the television on during the auto-adjust time frame (i.e., after the night threshold value and before the morning threshold value). For example, the threshold night value can be 8:00 p.m. and the threshold morning value can be 6:00 a.m. The viewer can turn the television and set-top box on at 9:00 p.m. In such embodiments, the system can be configured to automatically implement the blue light reduction instantly or implement the gradual reduction, starting with the original video signal and taking the predetermined period of time to gradually modify the signal to the full blue light reduction.

Figure 7:
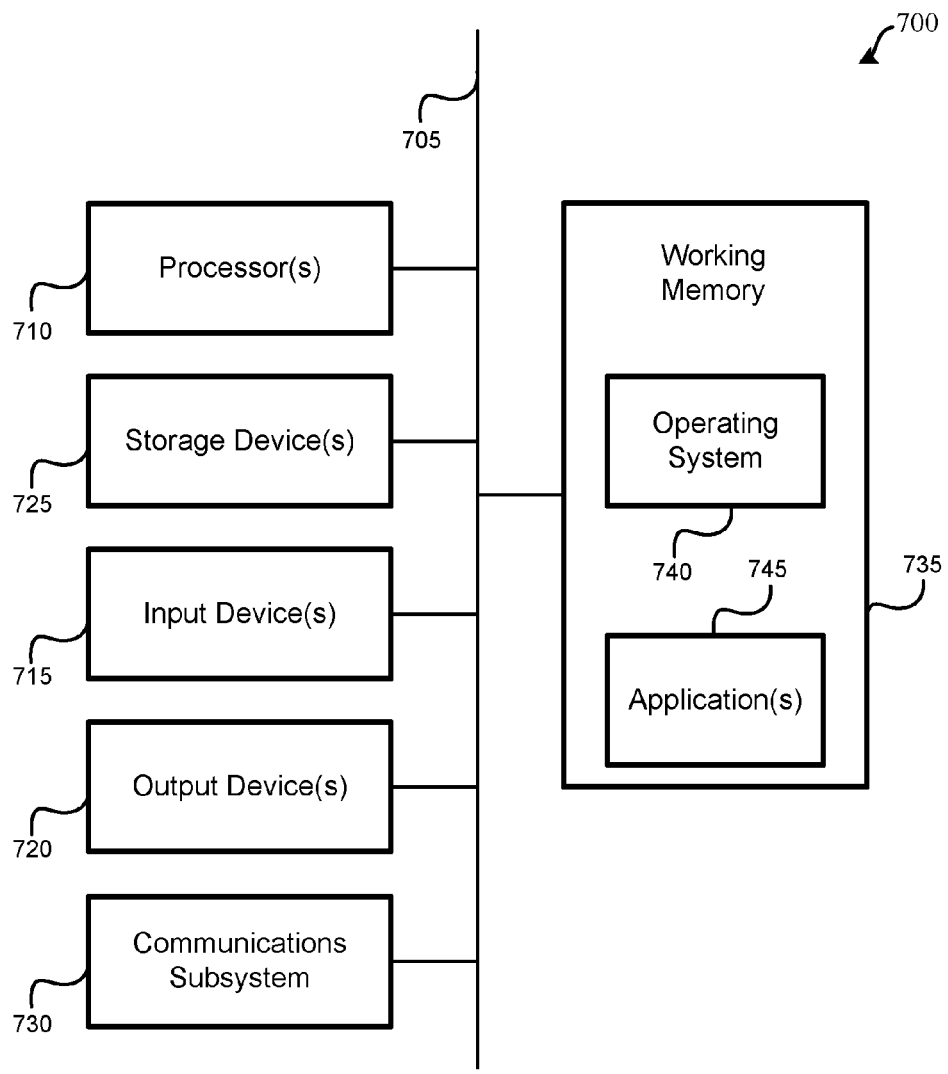
FIG. 7 illustrates an embodiment of a computer system.

FIG. 7 illustrates an embodiment of a computer system 700. A computer system 700 as illustrated in FIG. 7 may be incorporated into devices such as an STB (e.g., set-top box 200 of FIG. 2 and/or set-top box 310 of FIG. 3), a first electronic device, DVR, television, media system, personal computer, and the like. Moreover, some or all of the components of the computer system 700 may also be incorporated into a portable electronic device, mobile phone, or other device as described herein. FIG. 7 provides a schematic illustration of one embodiment of a computer system 700 that can perform some or all of the steps of the methods provided by various embodiments. It should be noted that FIG. 7 is meant only to provide a generalized illustration of various components, any or all of which may be utilized as appropriate. FIG. 7, therefore, broadly illustrates how individual system elements may be implemented in a relatively separated or relatively more integrated manner.

The computer system 700 is shown comprising hardware elements that can be electrically coupled via a bus 705, or may otherwise be in communication, as appropriate. The hardware elements may include one or more processors 710, including without limitation one or more general-purpose processors and/or one or more special-purpose processors such as digital signal processing chips, graphics acceleration processors, and/or the like; one or more input devices 715, which can include without limitation a mouse, a keyboard, a camera, and/or the like; and one or more output devices 720, which can include without limitation a display device, a printer, and/or the like.

The computer system 700 may further include and/or be in communication with one or more non-transitory storage devices 725, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like.

The computer system 700 might also include a communications subsystem 730, which can include without limitation a modem, a network card (wireless or wired), an infrared communication device, a wireless communication device, and/or a chipset such as a Bluetooth™ device, an 802.11 device, a WiFi device, a WiMax device, cellular communication facilities, etc., and/or the like. The communications subsystem 730 may include one or more input and/or output communication interfaces to permit data to be exchanged with a network such as the network described below to name one example, other computer systems, television, and/or any other devices described herein. Depending on the desired functionality and/or other implementation concerns, a portable electronic device or similar device may communicate image and/or other information via the communications subsystem 730. In other embodiments, a portable electronic device, e.g. the first electronic device, may be incorporated into the computer system 700, e.g., an electronic device or STB, as an input device 715. In many embodiments, the computer system 700 will further comprise a working memory 735, which can include a RAM or ROM device, as described above.

The computer system 700 also can include software elements, shown as being currently located within the working memory 735, including an operating system 740, device drivers, executable libraries, and/or other code, such as one or more application programs 745, which may comprise computer programs provided by various embodiments, and/or may be designed to implement methods, and/or configure systems, provided by other embodiments, as described herein. Merely by way of example, one or more procedures described with respect to the methods discussed above, such as those described in relation to FIG. 5 or 6, might be implemented as code and/or instructions executable by a computer and/or a processor within a computer; in an aspect, then, such code and/or instructions can be used to configure and/or adapt a general purpose computer or other device to perform one or more operations in accordance with the described methods.

A set of these instructions and/or code might be stored on a non-transitory computer-readable storage medium, such as the storage device(s) 725 described above. In some cases, the storage medium might be incorporated within a computer system, such as computer system 700. In other embodiments, the storage medium might be separate from a computer system e.g., a removable medium, such as a compact disc, and/or provided in an installation package, such that the storage medium can be used to program, configure, and/or adapt a general purpose computer with the instructions/code stored thereon. These instructions might take the form of executable code, which is executable by the computer system 700 and/or might take the form of source and/or installable code, which, upon compilation and/or installation on the computer system 700 e.g., using any of a variety of generally available compilers, installation programs, compression/decompression utilities, etc., then takes the form of executable code.

It will be apparent to those skilled in the art that substantial variations may be made in accordance with specific requirements. For example, customized hardware might also be used, and/or particular elements might be implemented in hardware, software including portable software, such as applets, etc., or both. Further, connection to other computing devices such as network input/output devices may be employed.

As mentioned above, in one aspect, some embodiments may employ a computer system such as the computer system 700 to perform methods in accordance with various embodiments of the technology. According to a set of embodiments, some or all of the procedures of such methods are performed by the computer system 700 in response to processor 710 executing one or more sequences of one or more instructions, which might be incorporated into the operating system 740 and/or other code, such as an application program 745, contained in the working memory 735. Such instructions may be read into the working memory 735 from another computer-readable medium, such as one or more of the storage device(s) 725. Merely by way of example, execution of the sequences of instructions contained in the working memory 735 might cause the processor(s) 710 to perform one or more procedures of the methods described herein. Additionally or alternatively, portions of the methods described herein may be executed through specialized hardware.

The terms "machine-readable medium" and "computer-readable medium," as used herein, refer to any medium that participates in providing data that causes a machine to operate in a specific fashion. In an embodiment implemented using the computer system 700, various computer-readable media might be involved in providing instructions/code to processor(s) 710 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the storage device(s) 725. Volatile media include, without limitation, dynamic memory, such as the working memory 735.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 710 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 700.

The communications subsystem 730 and/or components thereof generally will receive signals, and the bus 705 then might carry the signals and/or the data, instructions, etc. carried by the signals to the working memory 735, from which the processor(s) 710 retrieves and executes the instructions. The instructions received by the working memory 735 may optionally be stored on a non-transitory storage device 725 either before or after execution by the processor(s) 710.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the technology. Also, a number of steps may be undertaken before, during, or after the above elements are considered. Accordingly, the above description does not bind the scope of the claims.

As used herein and in the appended claims, the singular forms "a", "an", and "the" include plural references unless the context clearly dictates otherwise. Thus, for example, reference to "a user" includes a plurality of such users, and reference to "the processor" includes reference to one or more processors and equivalents thereof known to those skilled in the art, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed is:

1. A method for reducing a blue light component of displayed video, comprising:
   receiving, at a set-top box, a video signal having a white color balance, the white color balance including a red component value;
   adjusting, by the set-top box, the white color balance of the video signal by:
      when a current time reaches a predefined period of time before a threshold night value, gradually adjusting the white color balance of the video signal to increase the red component value to a set value incrementally over the predefined period of time,
      when the current time is after the threshold night value and before the predefined period of time before a threshold morning value, adjusting the white color balance of the video signal to maintain the red component value at the set value, and
      when the current time reaches the predefined period of time before the threshold morning value, gradually adjusting the white color balance of the video signal to decrease the red component value from the set value incrementally over the predefined period of time; and
   transmitting, from the set-top box, the video signal with the adjusted white color balance to a display device.

2. The method for reducing the blue light component of displayed video of claim 1, when the current time reaches the threshold night value, the red component value is a configured maximum value.

3. The method for reducing the blue light component of displayed video of claim 1, further comprising:
   providing, by the set-top box, a user interface for configuring one or more parameters.

4. The method for reducing the blue light component of displayed video of claim 3, wherein the one or more parameters comprise:
   the threshold night value; and
   the threshold morning value.

5. The method for reducing the blue light component of displayed video of claim 3, wherein the one or more parameters comprise:
   the threshold night value;
   the threshold morning value;
   the predefined period of time; and
   the set value.

6. The method for reducing the blue light component of displayed video of claim 1, wherein the white color balance of the video signal adjusted to increase the red component value has a blue component value insufficient to disrupt the circadian rhythm of a human.

7. A system for reducing a blue light component of displayed video, comprising:
   a processor; and
   a memory, the memory containing instructions that, when executed by the processor, cause the processor to:

receive a video signal having a white color balance, the white color balance including a red component value;

adjust the white color balance of the video signal by:
when a current time reaches a predefined period of time before a threshold night value, gradually adjust the white color balance of the video signal to increase the red component value to a set value incrementally over the predefined period of time,
when the current time is after the threshold night value and before the predefined period of time before a threshold morning value, adjust the white color balance of the video signal to maintain the red component value at the set value, and
when the current time reaches the predefined period of time before the threshold morning value, gradually adjust the white color balance of the video signal to decrease the red component value from the set value incrementally over the predefined period of time; and transmit the video signal with the adjusted white color balance to a display device.

8. The system for reducing the blue light component of displayed video of claim 7, wherein when the current time reaches the threshold night value, the red component value is a maximum value and a blue component value of the white color balance is a minimum value.

9. The system for reducing the blue light component of displayed video of claim 7, wherein the instructions comprise further instructions that cause the processor to:
provide a user interface for configuring one or more parameters.

10. The system for reducing the blue light component of displayed video of claim 9, wherein the one or more parameters comprise:
the threshold night value; and
the threshold morning value.

11. The system for reducing the blue light component of displayed video of claim 9, wherein the one or more parameters comprise:
the threshold night value;
the threshold morning value;
the predefined period of time; and
the set value.

12. The system for reducing the blue light component of displayed video of claim 7, wherein the white color balance of the video signal adjusted to increase the red component value has a blue component value insufficient to disrupt the circadian rhythm of a human.

13. A machine-readable storage device having stored thereon instructions for reducing the blue light component of displayed video, the instructions causing one or more processors to perform operations, including:
receiving a video signal having a white color balance, the white color balance including a red component value;
adjusting the white color balance of the video signal by:
when a current time reaches a predefined period of time before a threshold night value, gradually adjusting the white color balance of the video signal to increase the red component value to a set value incrementally over the predefined period of time,
when the current time is after the threshold night value and before the predefined period of time before a threshold morning value, adjusting the white color balance of the video signal to maintain the red component value at the set value, and
when the current time reaches the predefined period of time before the threshold morning value, gradually adjusting the white color balance of the video signal to decrease the red component value from the set value incrementally over the predefined period of time; and transmitting the video signal with the adjusted white color balance to a display device.

14. The machine-readable storage device of claim 13, wherein at an end of the predefined period of time the red component value is a maximum value and a blue component value of the white color balance is a minimum value.

15. The machine-readable storage device of claim 13, having stored thereon instructions for causing one or more processors to perform further operations, including:
providing a user interface for configuring one or more parameters, wherein the one or more parameters comprise:
the threshold night value; and
the threshold morning value.

16. The machine-readable storage device of claim 13, having stored thereon instructions for causing one or more processors to perform further operations, including:
providing a user interface for configuring one or more parameters, wherein the one or more parameters comprise:
the threshold night value;
the threshold morning value;
the predefined period of time; and
the set value.

17. The machine-readable storage device of claim 13, wherein the white color balance of the video signal adjusted to increase the red component value has a blue component value insufficient to disrupt the circadian rhythm of a human.

18. The method for reducing the blue light component of displayed video of claim 1, wherein adjusting the white color balance of the video signal to increase the red component value to a set value comprises reducing the blue component value.

19. The system for reducing the blue light component of displayed video of claim 7, wherein adjusting the white color balance of the video signal to increase the red component value to a set value comprises reducing the blue component value.

20. The machine-readable storage device of claim 13, wherein adjusting the white color balance of the video signal to increase the red component value to a set value comprises reducing the blue component value.

* * * * *